US 6,560,490 B2

(12) United States Patent
Grill et al.

(10) Patent No.: US 6,560,490 B2
(45) Date of Patent: May 6, 2003

(54) WAVEFORMS FOR SELECTIVE STIMULATION OF CENTRAL NERVOUS SYSTEM NEURONS

(75) Inventors: Warren M. Grill, Cleveland Heights, OH (US); Cameron C. McIntyre, Marietta, OH (US)

(73) Assignee: Case Western Reserve University, Cleveland, OH (US)

( * ) Notice: Subject to any disclaimer, the term of this patent is extended or adjusted under 35 U.S.C. 154(b) by 174 days.

(21) Appl. No.: 09/799,272

(22) Filed: Mar. 5, 2001

(65) Prior Publication Data

US 2002/0123780 A1 Sep. 5, 2002

Related U.S. Application Data

(60) Provisional application No. 60/235,417, filed on Sep. 26, 2000.

(51) Int. Cl.$^7$ .................................................. A61N 1/40
(52) U.S. Cl. ........................ 607/72; 607/45; 607/74
(58) Field of Search ...................... 607/5, 9, 14, 45, 607/46, 58, 57, 56, 53, 54, 63, 62, 61, 72, 74, 75, 118, 544, 545

(56) References Cited

U.S. PATENT DOCUMENTS

| | | | | |
|---|---|---|---|---|
| 5,025,807 A | * | 6/1991 | Zabara | 607/45 |
| 5,411,540 A | | 5/1995 | Edell et al. | |
| 5,458,625 A | * | 10/1995 | Kendall | 607/46 |
| 5,755,750 A | | 5/1998 | Petruska et al. | 607/75 |
| 5,944,747 A | | 8/1999 | Greenberg et al. | |
| 6,295,470 B1 | * | 9/2001 | Mower | 607/14 |
| 2002/0077670 A1 | * | 6/2002 | Archer et al. | 607/45 |

OTHER PUBLICATIONS

"Intelligent Systems and Technologies in Rehabilitation Engineering" (2001 by CRC Press LLC—Edited by Teodorescu & Jain).
"Model–Based Design of Stimulus Waveforms for Selective Microstimulation in the Central Nervous System" from "Proceedings of the 21st Annual Intl. Conference of the IEEE Engineering in Medicine and Biology Society" p. 384 (Case Western Reserve University, Cleveland, OH –Dept. of Biomedical Engineering) Oct. 1999.
"Selective Microstimulation of Central Nervous System Neurons" from Annals of Biomedical Engineering, vol. 28, pp. 219–233, 2000 (Case Western Reserve University, Cleveland, OH —Dept. of Biomedical Engineering).

* cited by examiner

Primary Examiner—Tu Ba Hoang
(74) Attorney, Agent, or Firm—Fay, Sharpe, Fagan, Minnich & McKee, LLP

(57) ABSTRACT

Asymmetric charge-balanced stimulation waveforms are defined and used for CNS stimulation with selective stimulation of either neuronal cell bodies or axon fibers of passage in favor of the other. A pre-pulse is followed by an opposite polarity stimulation pulse, with the pre-pulse being relatively low-amplitude and long-duration as compared to the stimulation pulse. The pre-pulse and stimulation pulse are charge-balanced to prevent tissue damage and electrode corrosion. The polarity of the pre-pulse and stimulation pulse control the selectivity of stimulation with respect to neuronal cell bodies versus axon fibers of passage. The waveform used in the stimulation method optionally includes a zero-amplitude phase having a duration of 0 to 500 microseconds.

21 Claims, 6 Drawing Sheets

WAVEFORMS FOR SELECTIVE STIMULATION OF CENTRAL NERVOUS SYSTEM NEURONS

CROSS-REFERENCE TO RELATED APPLICATION

This application claims priority from and hereby expressly incorporates by reference U.S. provisional application No. 60/235,417 filed Sep. 26, 2000.

REFERENCE TO FEDERALLY SPONSORED FUNDING

Research for the technology described and claimed herein was at least partially funded by the National Science Foundation, BES9709488, Sep. 15, 1997–Aug. 31, 2000.

BACKGROUND OF THE INVENTION

The present invention relates generally to electrical stimulation of the human central nervous system for treatment of neurological disorders in humans and other mammals. It is necessary to achieve the desired effect(s) that stimuli applied in the central nervous system activate the targeted elements (those neural elements, either local cells or axons of passage, that produce the desired effect(s)) without activation of the non-targeted neural elements (those neural elements, either local cells or axons of passage, that produce undesired effect(s) or do not produce the desired effect(s)). Thus, the ability to activate (stimulate) selectively either local neuron cells or axons of passage is required for device efficacy.

Monophasic cathodic stimuli have enabled some selective stimulation of axons of passage over local cells in CNS tissue. This is illustrated graphically in FIG. 1 wherein the line AF represents percent activation of axons of passage (fibers) and the line AC represents percentage activation of local neuronal cells for a given stimulus amplitude (pulse duration (pd=0.20 milliseconds (ms). As shown, activation of 70% of fibers is possible with activation of only 10% of local cells. Conversely, monophasic anodic stimuli have enabled some selective stimulation of local cells over fibers. This phenomenon is illustrated graphically in FIG. 2, again using the lines AF and AC to represent percent activation of fibers and local cells in a given sample of CNS tissue depending upon stimulus amplitude (pd=0.20 ms). Here, activation of 70% of the cells is possible with activation of only 25% of the fibers. Unfortunately, as is well known in the art, monophasic stimuli are not usable in practice owing to the fact that the stimuli are not charge-balanced, a fact that leads to tissue damage and electrode corrosion.

Use of symmetric, charge-balanced stimuli greatly decreases selectively. The effects of using an anodic first pulse (pd=0.20 ms) immediately followed by a cathodic second pulse (pd=0.20 ms) are shown in FIG. 3, wherein the lines AF and AC represent percent activation of fibers and local cells, respectively. It can be seen that a stimulus amplitude that activated 70% of the fibers also activated 15% of local cells. The effects of using a cathodic first pulse (pd=0.20 ms) immediately followed by an anodic second pulse (pd=0.2. ms) are shown in FIG. 4 by the lines AF and AC that represent percent activation of fibers and local cells, respectively. A stimulus amplitude sufficient to activate 70% of the cells also activated 100% of fibers of passage.

In light of the foregoing deficiencies and others associated with known techniques for obtaining either selective activation of axons of passage (fibers) over local cells, or for obtaining selective activation of local cells over fibers, a need has been identified for a novel and unobvious method and apparatus for selective stimulation (activation) of CNS neurons, i.e., stimulation of local neuron cells with minimal stimulation of axons of passage or stimulation of axons of passage with minimal stimulation of local neuron cells.

SUMMARY OF THE INVENTION

Asymmetric charge-balanced stimulation waveforms are defined and used for CNS stimulation with selective stimulation of either axons neuronal cell bodies or axon fibers of passage in favor of the other. A pre-pulse is followed by an opposite polarity stimulation pulse, with the pre-pulse being relatively low-amplitude and long-duration as compared to the stimulation pulse. The pre-pulse and stimulation pulse are charge-balanced to prevent tissue damage and electrode corrosion. The polarity of the pre-pulse and stimulation pulse control the selectivity of stimulation with respect to neuronal cell bodies versus axon fibers of passage. The waveform used in the stimulation method optionally includes a zero-amplitude phase having a duration of 0 to 500 microseconds.

One advantage of the present invention resides in the provision of waveforms for selective stimulation of central nervous system neurons.

Another advantage of the present invention is found in the provision of a method and apparatus for applying stimuli in the central nervous system to activate the targeted elements (those neural elements, either local cells or axons of passage, that produce the desired effect(s)) without activation of the non-targeted neural elements (those neural elements, either local cells or axons of passage, that produce undesired effect(s) or do not produce the desired effect(s)).

Still other benefits and advantages of the invention will become readily apparent to one of ordinary skill in the art to which the invention pertains upon reading this specification.

BRIEF DESCRIPTION OF THE DRAWINGS

The invention comprises a plurality of components and arrangements of components, and a variety of steps and arrangements of steps, preferred embodiments of which are disclosed herein and illustrated in the accompanying drawings, wherein.

DETAILED DESCRIPTION OF PREFERRED EMBODIMENTS

Figure 1:
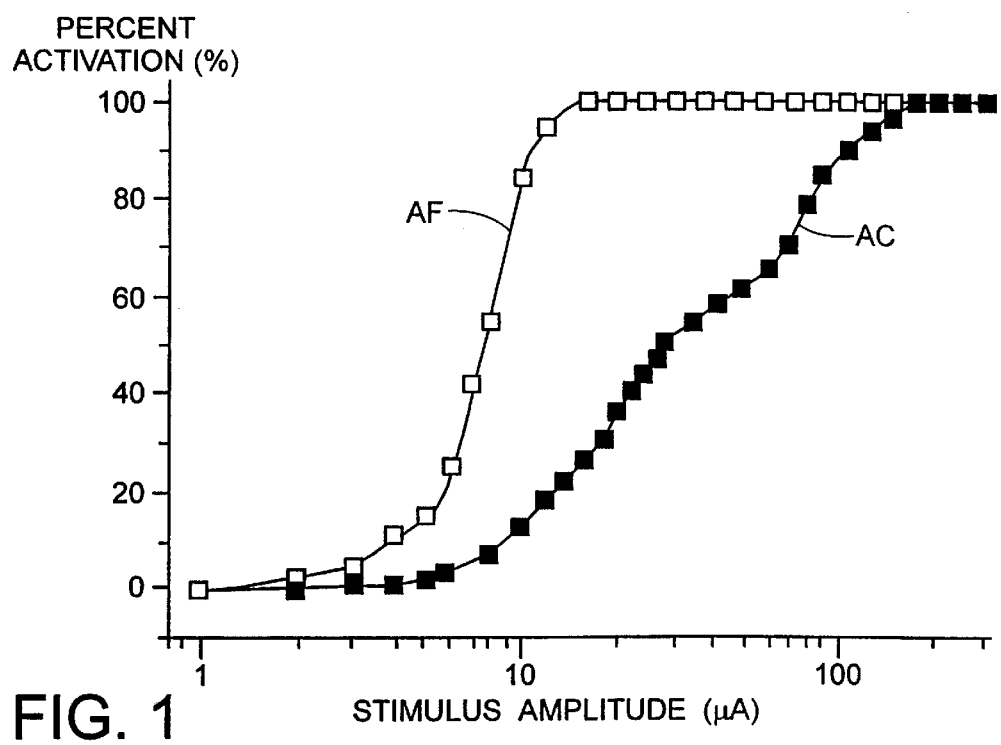
FIG. 1 graphically illustrates percent activation of local cells and axons of passage (fibers) in CNS tissue using a monophasic cathodic stimulus pulse of varying amplitude (pulse duration=0.20 milliseconds)
Figure 2:
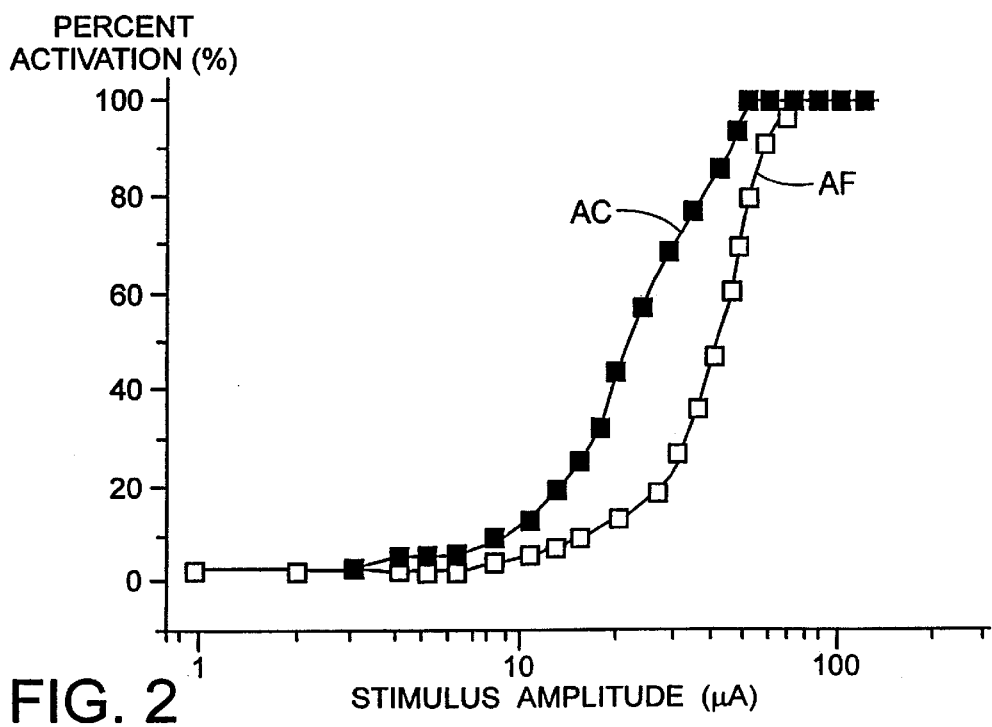
FIG. 2 graphically illustrates percent activation of local cells and axons of passage (fibers) in CNS tissue using a monophasic anodic stimulus pulse of varying amplitude (pulse duration=0.20 milliseconds)
Figure 3:
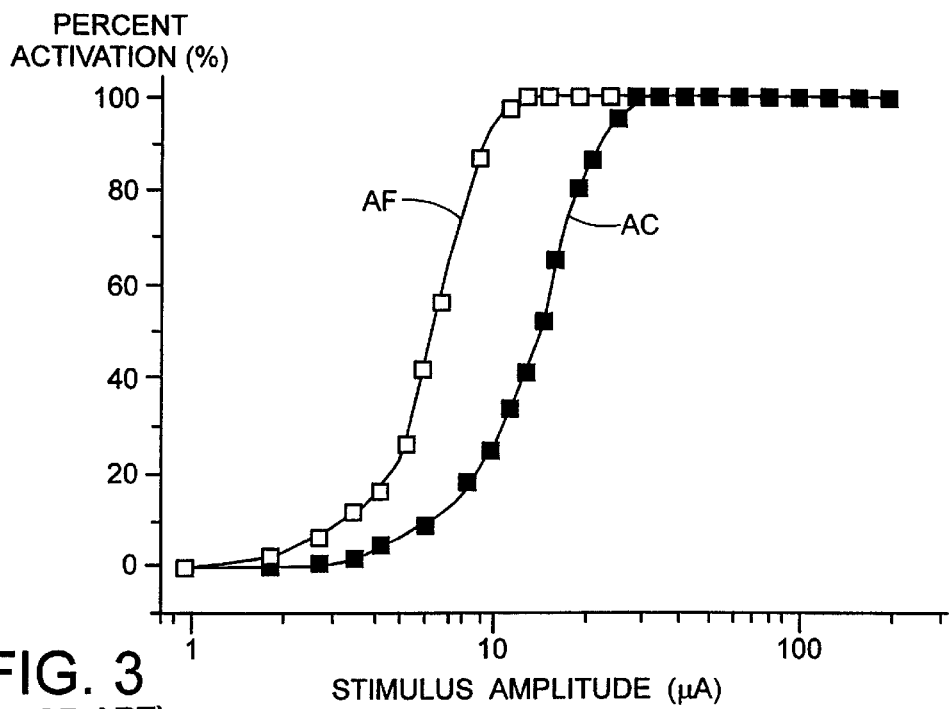
FIG. 3 graphically illustrates percent activation of local cells and axons of passage (fibers) in CNS tissue using a symmetric, charge-balanced, biphasic stimulus pulse (anodic first pulse) of varying amplitude (pulse duration=0.20 milliseconds)
Figure 4:
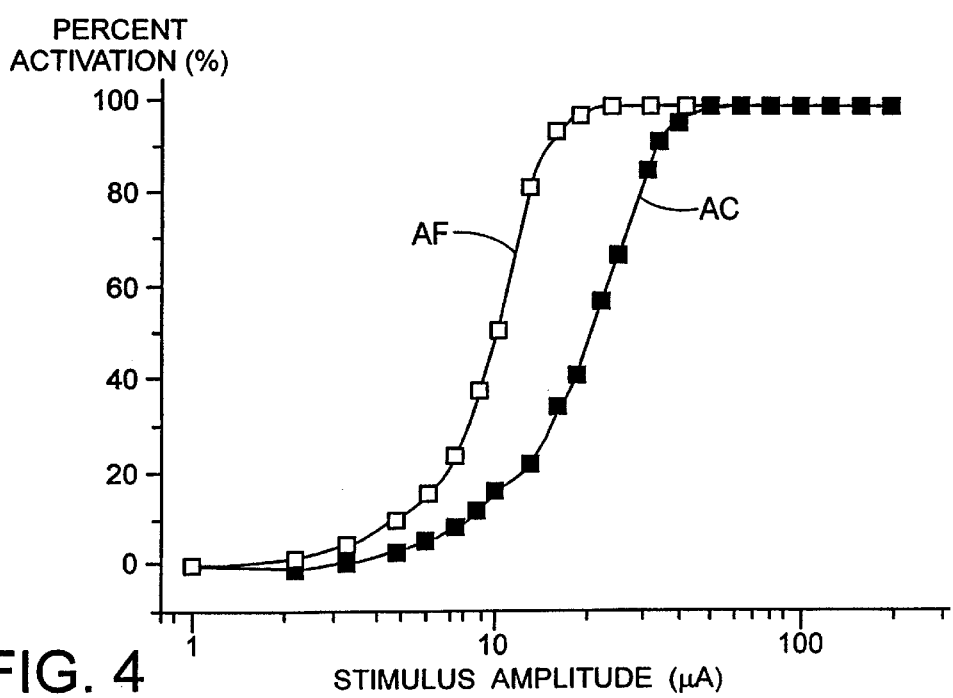
FIG. 4 graphically illustrates percent activation of local cells and axons of passage (fibers) in CNS tissue using a symmetric, charge-balanced, biphasic stimulus pulse (cathodic first pulse) of varying amplitude (pulse duration=0.20 milliseconds)
Figure 5:
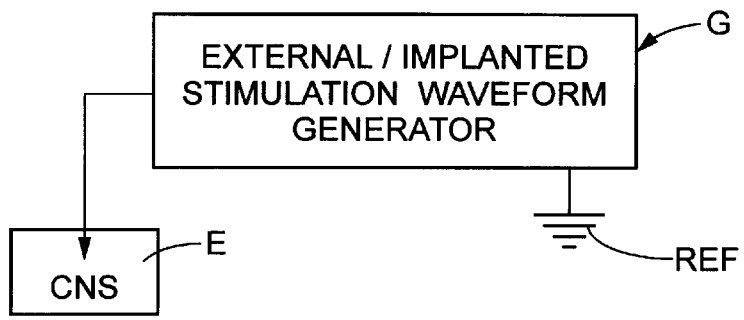
FIG. 5 diagrammatically illustrates a stimulation waveform generator adapted for selective stimulation of central nervous system neurons in accordance with the present invention.

Referring to FIG. 5, a stimulation waveform generator G is diagrammatically illustrated. The hardware of the generator G is conventional. Likewise, a conventional electrode E, such as a metal microelectrode or a multiple-contact electrode, is inserted into the desired location in the brain or spinal cord (shown as "CNS" in FIG. 5). The generator G, itself, can be external to the human or other mammal. When implanted, a metal case of the generator G can act as a reference electrode. Alternatively, the electrode E is bi-polar and includes a reference electrode as a part thereof. If the electrode E is mono-polar, a separate reference electrode REF may be implanted into the central nervous system CNS or elsewhere in the body of the human or other mammal to be stimulated if the case of the stimulator is not used as a reference electrode.

Unlike known stimulation generators, the stimulation waveform generator G is configured or programmed to output novel and unobvious stimulation waveforms in accordance with the present invention. A method for generating a first waveform in accordance with the present invention using the generator G is disclosed in FIG. 6. An example of a first waveform generated in accordance with the method described in FIG. 6 is illustrated at WVC in FIG. 7 and is particularly adapted for selective stimulation of local cells over axons of passage (fibers) in CNS tissue.

Figure 6:
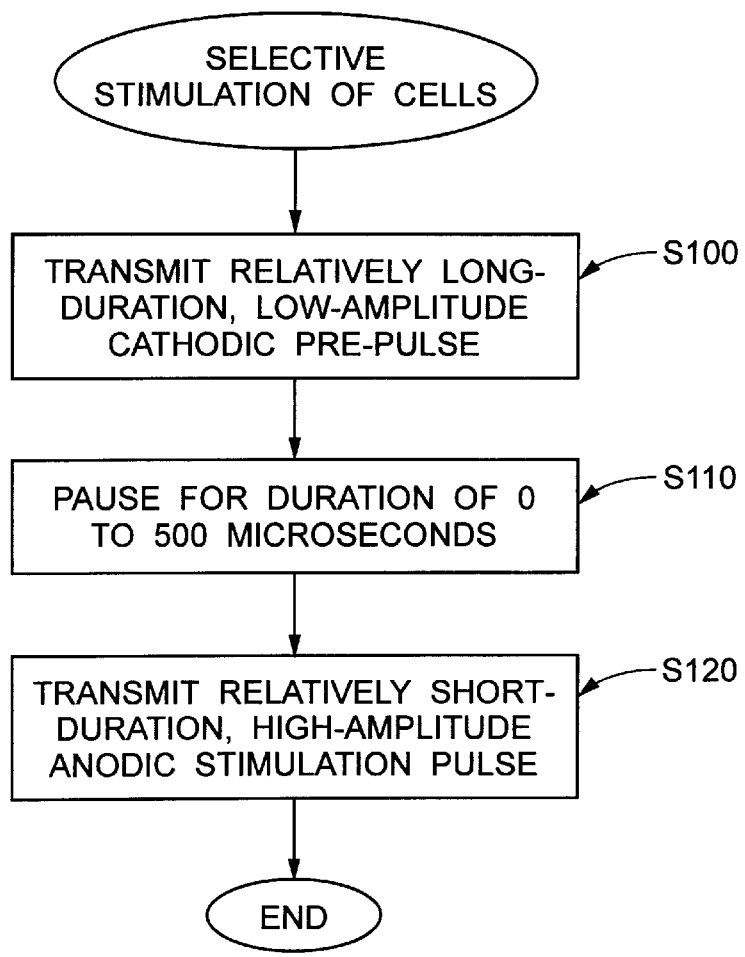
FIG. 6 is a flow chart that illustrates a method for selective stimulation of local cells in CNS tissue according to the present invention.
Figure 7:
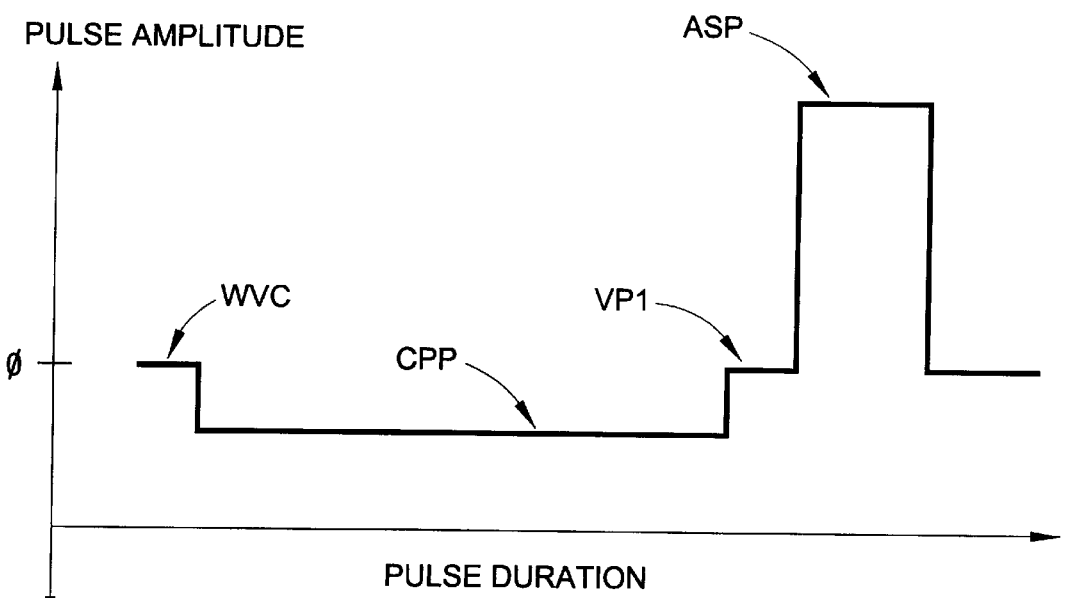
FIG. 7 graphically illustrates a waveform generated in accordance with the method disclosed in FIG. 6.

Referring to both FIGS. 6 and 7, the method for selective stimulation of local cells in CNS tissue comprises a step S100 of generating a relatively long-duration, low-amplitude cathodic pre-pulse CPP. This cathodic pre-pulse has the effect of increasing the excitability of the local neuronal cells and decreasing the excitability of the axonal fibers in CNS tissue, without acting as a stimulation pulse that is intended to evoke the desired CNS response. Subsequent to the step S100, the method comprises a step S110 of pausing with no stimulation amplitude as shown at VP1 in FIG. 7. It is most preferred that this pause VP1 last from 0 and 500 microseconds. After the step S110, the method comprises a step S120 of transmitting a relatively short-duration, high-amplitude anodic stimulation pulse ASP after which the amplitude of the waveform WVC returns to 0. The anodic stimulation pulse ASP is intended to evoke the desired CNS response.

The cathodic pre-pulse CPP is relatively long compared to the anodic stimulation pulse ASP. In one embodiment, the duration of the cathodic pre-pulse is 8 to 12 times the duration of the anodic stimulation pulse. For example, a cathodic pre-pulse CPP having a pulse duration pd=1.00 millisecond (ms) and an anodic stimulation pulse ASP having a pulse duration pd=0.10 ms can be used in accordance with the present invention. To preserve charge-balancing, the charge delivered by the cathodic pre-pulse CPP is equal in magnitude and opposite in polarity relative to the charge delivered by the anodic stimulation pulse ASP.

Figure 8:
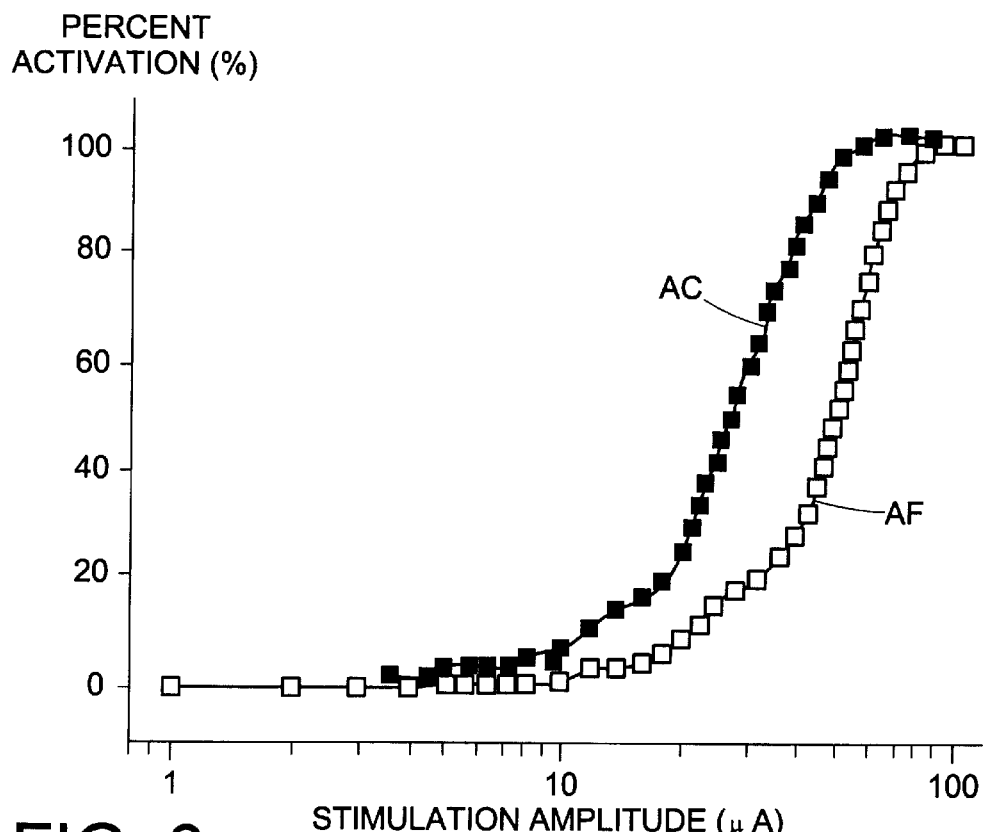
FIG. 8 graphically illustrates percent activation of local cells and axons of passage (fibers) in CNS tissue using an example stimulus pulse generated according to the method disclosed in FIG. 6 depending upon the amplitude of the anodic stimulation pulse.

FIG. 8 graphically illustrates percent activation of fibers AF and percent activation of cells AC using a stimulation waveform WVC generated in accordance with the method of FIG. 6. It can be seen that an anodic stimulation pulse ASP having an amplitude (approximately 35 μA) sufficient to activate 70% of local cells activated only 20% of fibers.

Figure 9:
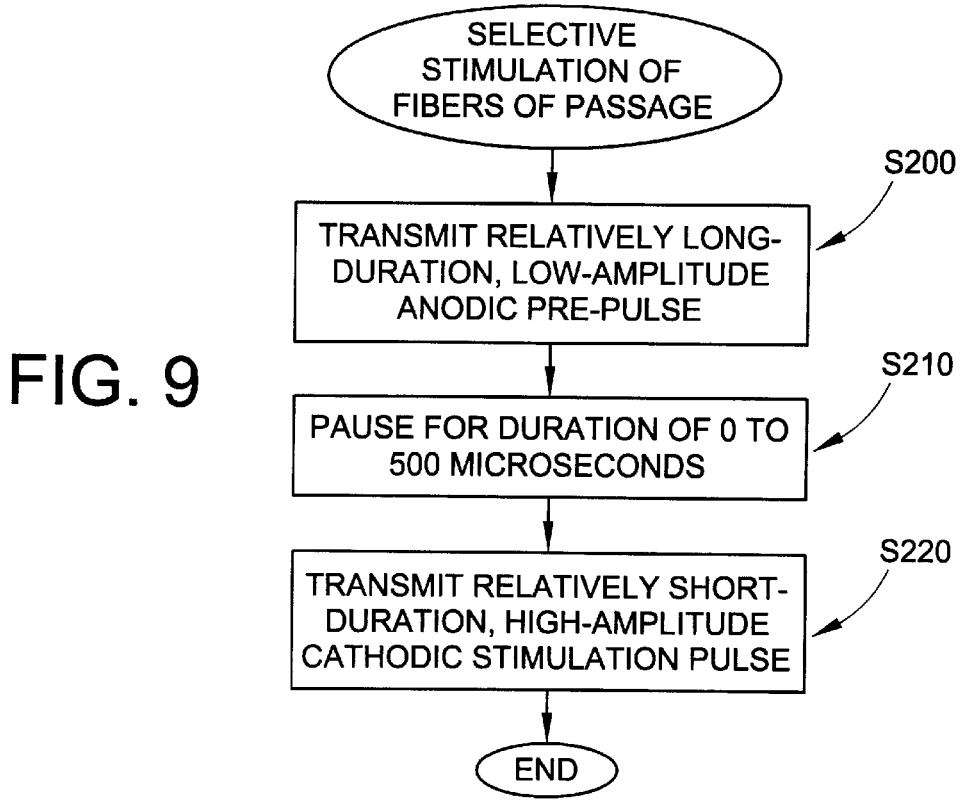
FIG. 9 is a flow chart that illustrates a method for selective stimulation of fibers in CNS tissue according to the present invention.

A method for generating a second waveform in accordance with the present invention using the generator G is disclosed in FIG. 9. An example of a second waveform generated in accordance with the method described in FIG. 9 is illustrated at WVF in FIG. 10 and is particularly adapted for selective stimulation of axon fibers of passage (fibers) over neuronal cell bodies in CNS tissue.

Figure 10:
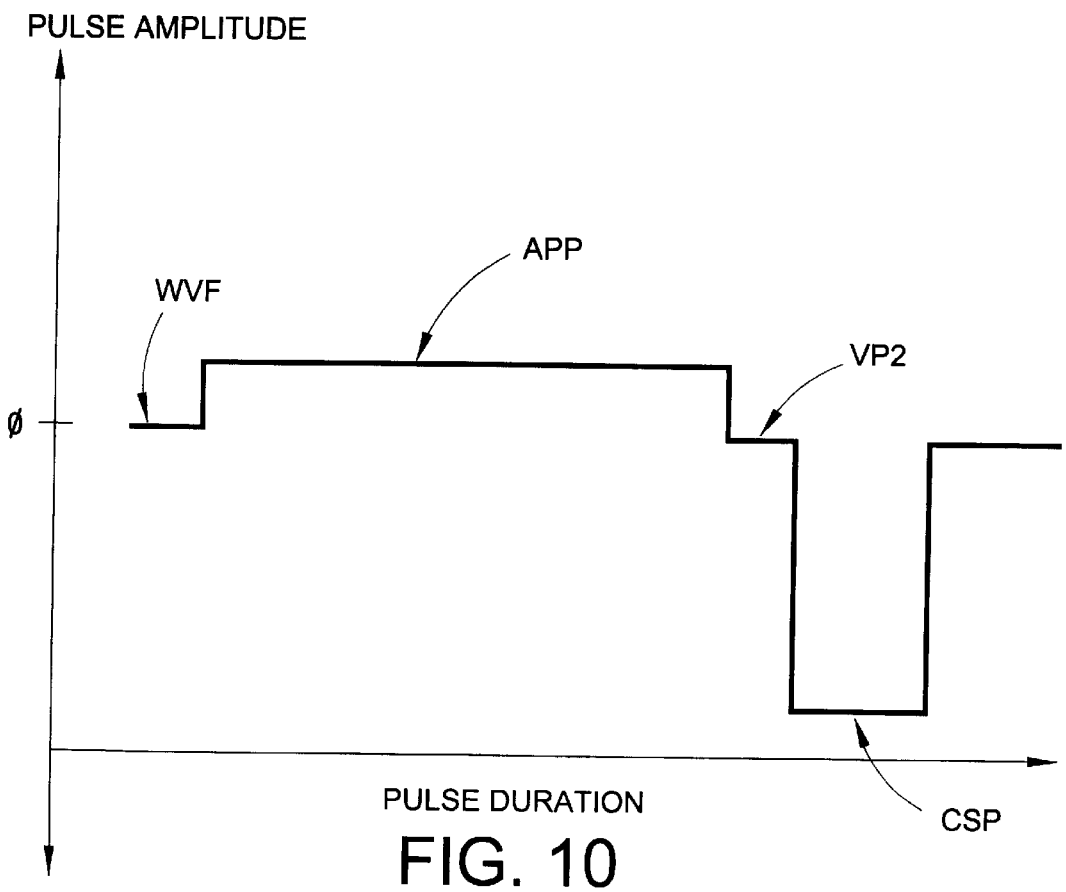
FIG. 10 graphically illustrates a waveform generated in accordance with the method disclosed in FIG. 9.

Referring to both FIGS. 9 and 10, the method for selective stimulation of fibers in CNS tissue comprises a step S200 of generating a relatively long-duration, low-amplitude anodic pre-pulse APP. This anodic pre-pulse has the effect of increasing the excitability of the axon fibers of passage and decreasing the excitability of the neuronal cell bodies in CNS tissue, without acting as a stimulation pulse that is intended to evoke the desired CNS response. Subsequent to the step S200, the method comprises a step S210 of pausing with no stimulation amplitude as shown at VP2 is FIG. 10. In a preferred embodiment, the pause VP2 has a duration of 0 to 500 microseconds. After the step S210, the method comprises a step S220 of transmitting a relatively short-duration, high-amplitude cathodic stimulation pulse CSP after which the amplitude of the waveform WVF returns to 0. The cathodic stimulation pulse CSP is intended to evoke the desired CNS response.

The anodic pre-pulse APP is relatively long compared to the cathodic stimulation pulse CSP. In one embodiment, the duration of the anodic pre-pulse is 8 to 12 times the duration of the cathodic stimulation pulse CSP. For example, an anodic pre-pulse APP having a pulse duration pd=0.20 ms and an cathodic stimulation pulse CSP having a pulse duration pd=0.02 ms can be used in accordance with the present invention. To preserve charge-balancing, the charge delivered by the anodic pre-pulse APP is equal in magnitude and opposite in polarity relative to the charge delivered by the cathodic stimulation pulse CSP.

Figure 11:
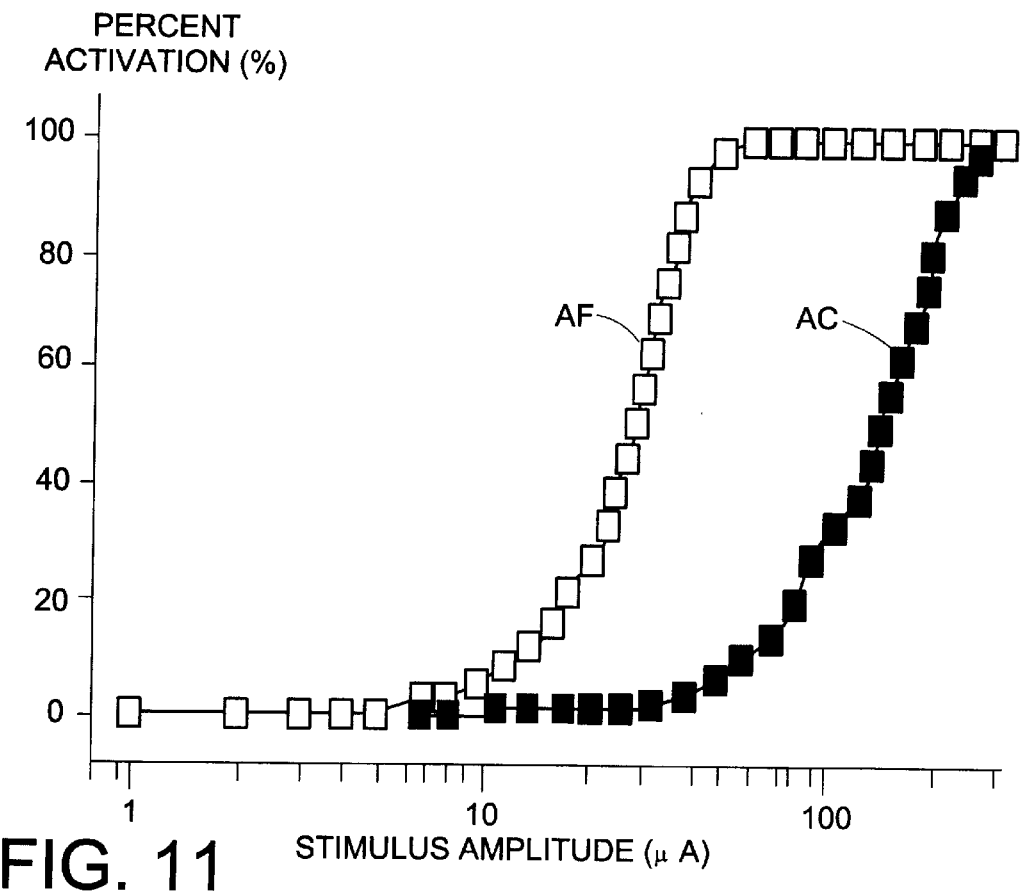
FIG. 11 graphically illustrates percent activation of local cells and axons of passage (fibers) in CNS tissue using an example stimulus pulse generated according to the method disclosed in FIG. 9 depending upon the amplitude of the cathodic stimulation pulse; and, FIG. 12 graphically illustrates percent activation of fibers as a function of percent activation of local cells for the waveforms.

FIG. 11 graphically illustrates percent activation of fibers AF and percent activation of cells AC using a stimulation waveform WVF generated in accordance with the method of FIG. 9. It can be seen that a cathodic stimulation pulse CSP having an amplitude (approximately 30 μA) sufficient to activate 70% of axon fibers of passage activated only 5% of neuronal cells.

Figure 12:
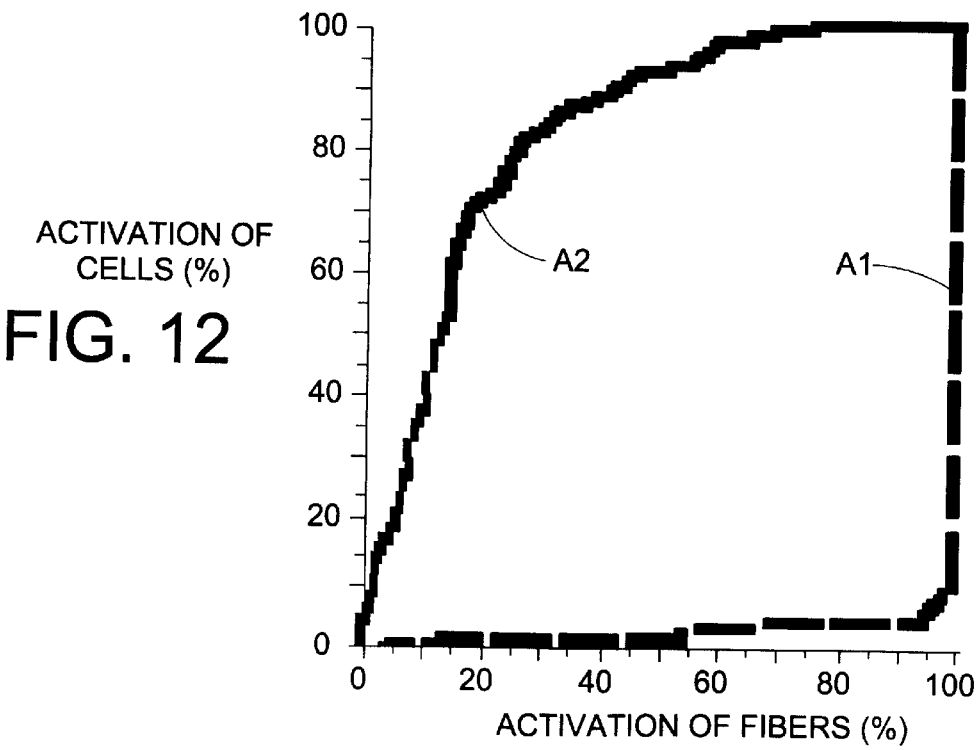

FIG. 12 illustrates percent activation of axon fibers of passage as a function of percent activation of neuronal cells using the waveforms WVC, WVF in accordance with the present invention. The line A1 represents possible activation of axon fibers of passage in favor of neuronal cells using the waveform WVF. Likewise, the line A2 represents possible activation of neuronal cells in favor of axon fibers of passage using the waveform WVC.

The first and second waveforms WVC,WVF have application in neural prosthetic devices that use electrodes places in the brain (e.g., visual or auditory prostheses or deep brain stimulation devices) or spinal cord (e.g., control of micturition or motor function).

Modifications and alterations will occur to those of ordinary skill in the art to which the invention pertains upon reading and understanding the foregoing disclosure. It is intended that the invention be construed as encompassing all such modifications and alterations insofar as they are encompassed by the following claims considered literally or according to the doctrine of equivalents.

Having thus described the preferred embodiments, what is claimed is:

1. An electrical waveform for stimulation of central nervous system tissue, said electrical waveform comprising:
    a pre-pulse phase having a first polarity, a first amplitude and a first duration, said first amplitude and first duration together defining a pre-pulse charge having a first magnitude and said first polarity; and,
    a stimulation-pulse phase following said pre-pulse phase, said stimulation-pulse phase having a second polarity opposite said first polarity, a second amplitude and second duration less than said first duration, said second amplitude and second duration together defining a stimulation charge having said second polarity and a second magnitude that equals said first magnitude.

2. The electrical waveform as set forth in claim 1, wherein said first duration is at least eight times longer than said second duration.

3. The electrical waveform as set forth in claim 2, wherein said first duration is at least eight times longer than said second duration and less than or equal to twelve times longer than said second duration.

4. The electrical waveform as set forth in claim 1, further comprising:
    a zero-amplitude phase located after said pre-pulse phase and before said stimulation-pulse phase, said zero-amplitude phase having a duration in the range of 0 to 500 microseconds.

5. The electrical waveform as set forth in claim 4, wherein said zero-amplitude phase is located immediately after said pre-pulse phase and immediately before said stimulation-pulse phase.

6. A method for selective electrical stimulation of central nervous system tissue, said method comprising:
    transmitting a pre-pulse phase of a stimulation waveform into central nervous system tissue through an electrode contacting said central nervous system tissue, said pre-pulse phase of said stimulation waveform having a first polarity, a first amplitude and a first duration, said first amplitude and first duration together defining a pre-pulse charge having a first magnitude and said first polarity; and,
    after said step of transmitting a pre-pulse phase of a stimulation waveform, transmitting a stimulation-pulse phase of said stimulation waveform into said central nervous system tissue through said electrode, said stimulation-pulse phase of said stimulation waveform having a second polarity opposite said first polarity, a second amplitude and second duration less than said first duration, said second amplitude and second duration together defining a stimulation charge having said second polarity and a second magnitude that equals said first magnitude.

7. The method as set forth in claim 6, wherein said first duration of said pre-pulse phase is at least eight times longer than said second duration of said stimulation-pulse phase.

8. The method as set forth in claim 7, wherein said first duration of said pre-pulse phase is at least eight times and no more than twelve times longer than said second duration of said stimulation-pulse phase.

9. The method as set forth in claim 6, further comprising:
    delaying for a select duration between said step of transmitting said pre-pulse phase and said step of transmitting said stimulation-pulse phase.

10. The method as set forth in claim 9, wherein said select duration is inclusively between 0 and 500 microseconds.

11. A method for selectively stimulating one of axons of passage and neuronal cells in favor of the other of axons of passage and neuronal cells in central nervous system tissue using electrical stimulation, said method comprising:
    transmitting a pre-pulse phase of an electrical waveform into central nervous system tissue through an electrode contacting said central nervous system tissue, said pre-pulse phase of said waveform having a first polarity, a first amplitude and a first duration, said first amplitude and first duration together defining a pre-pulse charge having a first magnitude and said first polarity; and,
    after said step of transmitting a pre-pulse phase, transmitting a stimulation-pulse phase of said waveform into said central nervous system tissue through said electrode, said stimulation-pulse phase of said waveform having a second polarity opposite said first polarity, a second amplitude and second duration less than said first duration, said second amplitude and second duration together defining a stimulation charge having said first magnitude and said second polarity.

12. The method as set forth in claim 11, wherein said pre-pulse phase is cathodic and said stimulation-pulse phase is anodic to effect stimulation of neuronal cells in favor of axons of passage.

13. The method as set forth in claim 11, wherein said pre-pulse phase is anodic and said stimulation-pulse phase is cathodic to effect stimulation of axons of passage in favor of neuronal cells.

14. The method as set forth in claim 11, wherein said first duration of said pre-pulse phase is at least eight times longer than said second duration of said stimulation-pulse phase.

15. The method as set forth in claim 14, wherein said first duration of said pre-pulse phase is at least eight times and no more than twelve times longer than said second duration of said stimulation-pulse phase.

16. The method as set forth in claim 11, further comprising:
    delaying for a select duration between said step of transmitting said pre-pulse phase and said step of transmitting said stimulation-pulse phase.

17. The method as set forth in claim 16, wherein said select duration is inclusively between 0 and 500 microseconds.

18. An apparatus for stimulating central nervous system tissue, said apparatus comprising:
    an electrode adapted for contact with central nervous system tissue; and,
    an electrical stimulation waveform generator electrically connected to said electrode, said waveform generator adapted to generate and output to said electrode a stimulation waveform comprising:
        a pre-pulse phase having a first polarity, a first amplitude and a first duration, said first amplitude and first duration together defining a pre-pulse charge having a first magnitude and said first polarity; and, a stimulation-pulse phase following said pre-pulse phase, said stimulation-pulse phase having a second polarity opposite said first polarity, a second amplitude and second duration less than said first duration, said second amplitude and second duration together defining a stimulation charge having said first magnitude and said second polarity.

19. The apparatus as set forth in claim 18, wherein said first duration is at least eight times longer than said second duration.

20. The apparatus as set forth in claim 19, wherein said first duration is at least eight times longer than said second duration and less than or equal to twelve times longer than said second duration.

21. The apparatus as set forth in claim 18, wherein said stimulation waveform further comprises:

a zero-amplitude phase located after said pre-pulse phase and before said stimulation-pulse phase, said zero-amplitude phase having a duration in the range of 0 to 500 microseconds.

* * * * *